(12) United States Patent
Nadikattu et al.

(10) Patent No.: US 11,094,420 B1
(45) Date of Patent: Aug. 17, 2021

(54) SYSTEM AND METHOD OF MAINTAINING SOCIAL DISTANCING GUIDELINES WITH NEARBY PERSONS

(71) Applicants: Rahul Reddy Nadikattu, San Jose, CA (US); Sikender Mohsienuddin Mohammad, Scottsdale, AZ (US)

(72) Inventors: Rahul Reddy Nadikattu, San Jose, CA (US); Sikender Mohsienuddin Mohammad, Scottsdale, AZ (US)

( * ) Notice: Subject to any disclaimer, the term of this patent is extended or adjusted under 35 U.S.C. 154(b) by 0 days.

(21) Appl. No.: 17/033,507

(22) Filed: Sep. 25, 2020

(51) Int. Cl.
| | |
|---|---|
| *G16H 50/30* | (2018.01) |
| *G08B 13/191* | (2006.01) |
| *A61B 5/01* | (2006.01) |
| *G06F 1/16* | (2006.01) |
| *G06N 20/00* | (2019.01) |
| *G06N 7/00* | (2006.01) |
| *G16H 50/20* | (2018.01) |

(52) U.S. Cl.
CPC ............ *G16H 50/30* (2018.01); *A61B 5/01* (2013.01); *G06F 1/163* (2013.01); *G06N 7/005* (2013.01); *G06N 20/00* (2019.01); *G08B 13/191* (2013.01); *G16H 50/20* (2018.01)

(58) Field of Classification Search
None
See application file for complete search history.

(56) References Cited

PUBLICATIONS

Nadikattu, Rahul Reddy, Sikender Mohsienuddin Mohammad, and Dr Whig. "Novel economical social distancing smart device for COVID19." International Journal of Electrical Engineering and Technology 11.4 (2020).*

Sathyamoorthy, Adarsh Jagan, et al. "COVID-robot: Monitoring social distancing constraints in crowded scenarios." arXiv preprint arXiv:2008.06585 (2020).*

Raghav, Sashmita, et al. "Suraksha: Low Cost Device to Maintain Social Distancing during CoVID-19." 2020 4th International Conference on Electronics, Communication and Aerospace Technology (ICECA). IEEE, 2020.*

Nguyen, Cong T., et al. "A comprehensive survey of enabling and emerging technologies for social distancing—Part II: Emerging technologies and open issues." IEEE Access 8 (2020): 154209-154236.*

* cited by examiner

*Primary Examiner* — G Steven Vanni

(57) ABSTRACT

A system and method of maintaining social distancing guidelines with nearby persons allows a user to receive a notification when other people enter within a perimeter around them. A wearable device, especially a belt, equipped with infrared (IR) sensors detects heat signatures of nearby objects. The wearable device subsequently relays this information to the user's mobile electronic device, immediately notifying the user of persons within the predefined radius. The wearable device further differentiates between different distinctly human heat signatures, using artificial intelligence to determine whether a nearby person has the elevated internal temperature that could be attributed to COVID-19, or if the person within the preset radius is asymptomatic. In this way, users may be alerted to dangers approaching from all sides. Users are participants in the global effort to reduce human exposure and help in reducing the distribution of cases to manageable levels.

10 Claims, 10 Drawing Sheets

SYSTEM AND METHOD OF MAINTAINING SOCIAL DISTANCING GUIDELINES WITH NEARBY PERSONS

FIELD OF THE INVENTION

The present invention relates generally to a public health maintenance system. More specifically, the method of maintaining social distancing guidelines with nearby persons relates to a system in which users may be alerted when others are within a radius of them. The present invention further notifies users of nearby persons who are showing symptoms of 2019 novel coronavirus (COVID-19).

BACKGROUND OF THE INVENTION

The year 2020 will surely forever be known as the year of the coronavirus. The global pandemic has dominated headlines around the world, affecting the rich and the poor equally. The spread of 2019 novel coronavirus (COVID-19) and many other such viruses is transmitted through contact between people through the air or on surfaces. For this reason, the three primary mechanisms for reducing the likelihood of catching COVID-19 as recommended by national and global health experts have been frequent washing of hands, wearing of masks when outdoors, and social isolation.

While the most effective of the three solutions, social isolation has also proven to be the most difficult. After several months of separation, many people become anxious and restless, leading to a decrease in compliance with COVID-19 isolation practices. Masks and handwashing are effective at mitigating risk, but the longer that the pandemic goes without a vaccine, the more dangerous it is to conduct necessary trips to the store or to work. What is needed is a wearable device that can further reduce risk of catching COVID-19 and other similarly-transmitted diseases. Further desirable is a method by which a user may be informed of nearby people who have non-visible symptoms of early COVID-19.

The present invention addresses these issues. More specifically, the method of maintaining social distancing guidelines with nearby persons enables a user to receive a notification when other people enter within a perimeter around them. A wearable device equipped with infrared (IR) sensors detects heat signatures of nearby objects. The wearable device subsequently relays this information to the user, immediately notifying the user of persons within the predefined radius. The wearable device further differentiates between different distinctly human heat signatures, using artificial intelligence to determine whether a nearby person has the elevated internal temperature that could be attributed to COVID-19.

DETAILED DESCRIPTION OF THE INVENTION

All illustrations of the drawings are for the purpose of describing selected versions of the present invention and are not intended to limit the scope of the present invention.

Figure 1:
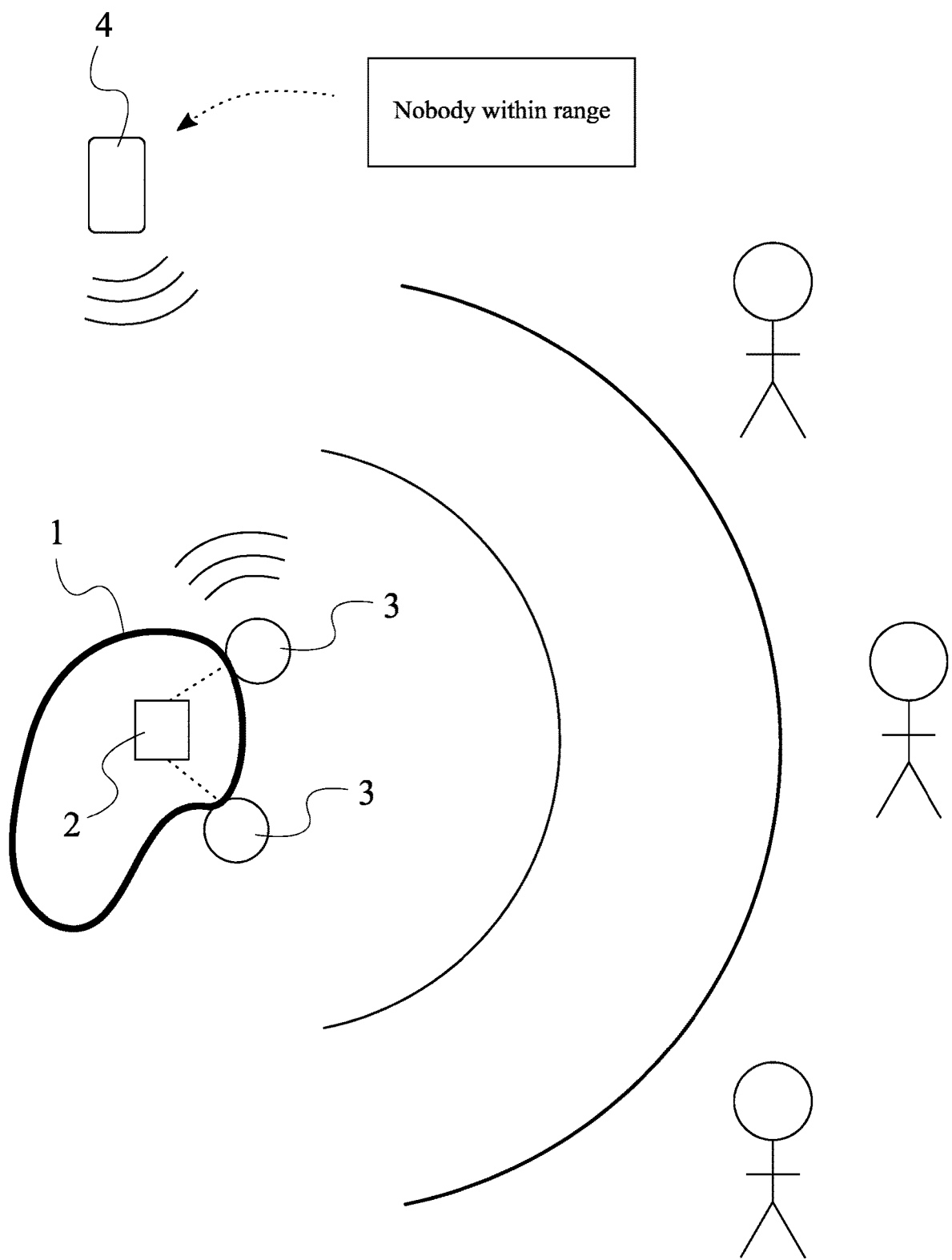
FIG. 1 is a schematic diagram illustrating the system of the present invention in a state of standard operation when people are outside of the active range.
Figure 2:
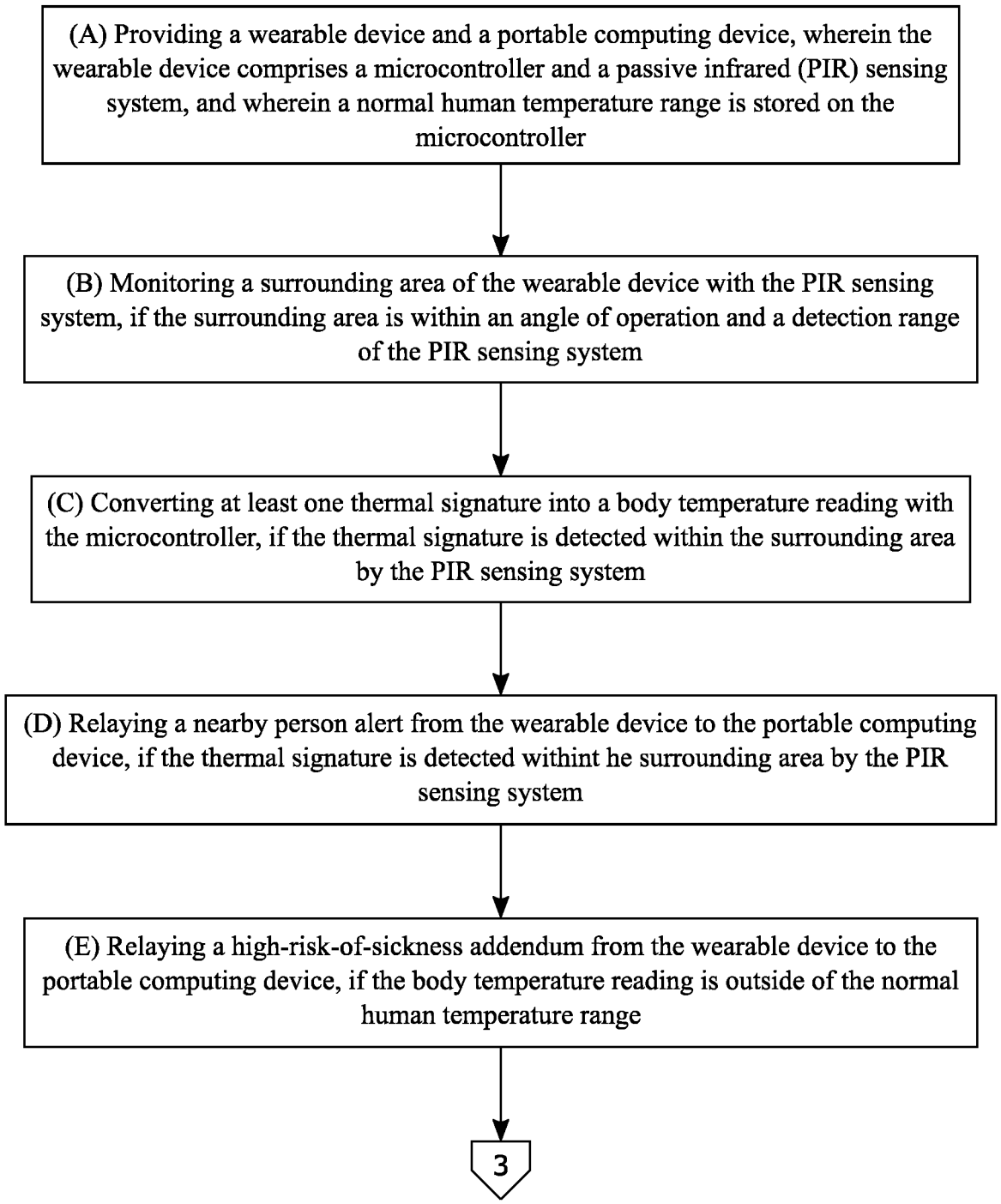
FIG. 2 is a flowchart illustrating the overall process for the method of the present invention.

The present invention is a system and method of maintaining social distancing guidelines with nearby persons that is used to reduce the spread of diseases, particularly the 2019 novel coronavirus (COVID-19). The present invention is configured to relay relevant information regarding the body temperatures of nearby persons, which can help in identifying and subsequently avoiding people experiencing fevers, as represented in FIG. 1. The system of the present invention includes a wearable device 1 and a portable computing device 4, wherein the wearable device 1 comprises a microcontroller 2 and a passive infrared (PIR) sensing system, and wherein a normal human temperature range is stored on the microcontroller 2 (Step A), as represented in FIG. 2. The wearable device 1 relates to a belt, wristwatch, necklace, or other such device capable of securing to the user. The portable computing device 4 may relate to any of smartphones, tablets, cell phones, or other such devices capable of wirelessly connecting the user to the wearable device 1. The microcontroller 2 allows the wearable device 1 to collect inputs from various sensors, to process and store information as necessary and appropriate, and to distribute information to parties in accordance with programmed instructions. The PIR sensing system 3 is a sensor, or an array of coordinated sensors, positioned to detect IR readings from their surroundings, to convert data into electronic signals, and to relay those signals to the microcontroller 2.

Figure 3:
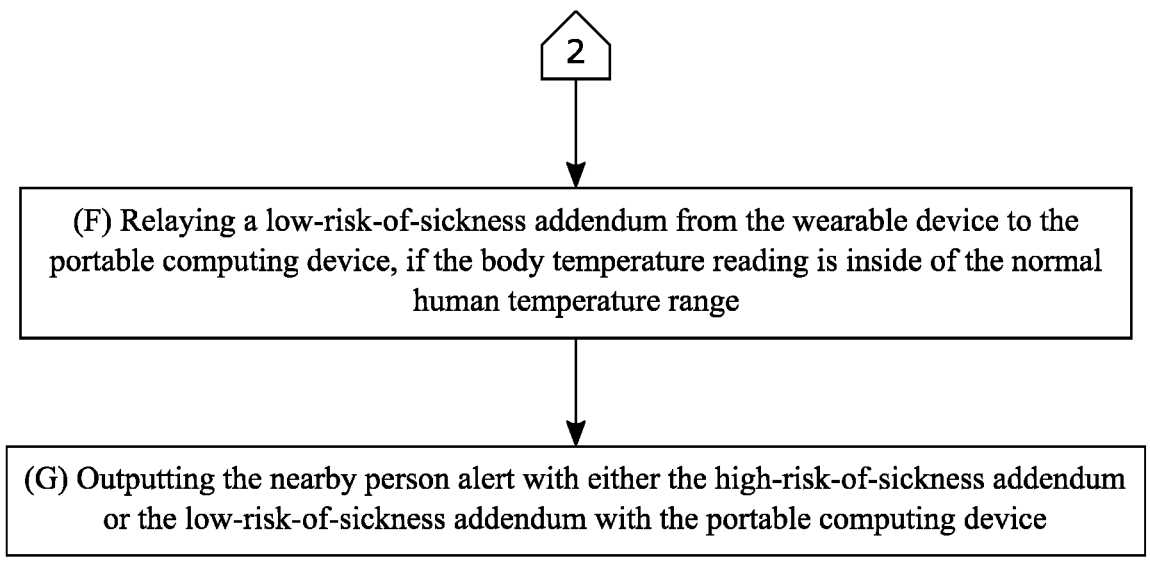
FIG. 3 is a continuation of FIG. 2.

The arrangement of features in the overall process of the present invention enables the user to detect nearby persons and determine whether those persons are at high risk of being ill. A surrounding area of the wearable device 1 is monitored with the PIR sensing system 3, if the surrounding area is within an angle of operation and a detection range of the PIR sensing system 3 (Step B). The surrounding area may be of a distance determined by the user or may be preset at a six-foot range to help the user follow COVID-19 social distancing guidelines. The angle of operation relates to the orientation of the PIR sensing system 3 relative to the user. The detection range describes the distance within which the present invention will alert the user of danger due to nearby persons. The PIR sensing system 3 coupled with the wearable device 1 enables the present invention to assist in avoiding situations in which disease is more likely to be spread. At least one thermal signature is converted into a body temperature reading with the microcontroller 2, if the thermal signature is detected within the surrounding area by the PIR sensing system 3 (Step C). The at least one thermal signature relates to the set of proximal objects or entities emitting significant heat, which can be initially processed to determine whether the signature is or is not from a human and can be subsequently processed to determine the body temperature reading of the human. A nearby person alert is next relayed from the wearable device 1 to the portable computing device 4, if the thermal signature is detected within the surrounding area by the PIR sensing system 3 (Step D). The microcontroller 2 processes the at least one thermal signature to compare the thermal signature to that of a human, thereby determining whether to notify the user. Subsequently, a high-risk-of-sickness addendum is relayed from the wearable device 1 to the portable computing device 4, if the body temperature reading is outside of the normal human temperature range (Step E). The microcontroller 2 uses artificial intelligence and machine learning algorithms to determine what temperatures are relevant for alerting purposes. Conversely, a low-risk-of-sickness addendum is relayed from the wearable device 1 to the portable computing device 4, if the body temperature reading is inside of the normal human temperature range (Step F), as represented in FIG. 3. Steps E and F ensure that the user knows the general status of nearby people and can act with increased urgency when required. Finally, the nearby person alert is outputted with either the high-risk-of-sickness addendum or the low-risk-of-sickness addendum with the portable computing device 4 (Step G). In this way, the user is notified of entities radiating heat comparable to that of a human and may react accordingly to dangerous situations.

The present invention assists users in staying safe while in public areas. It is often advantageous for the detection range to be a preset value associated with prevention of the spread of COVID-19. To this end, the detection range may be a six-foot radius centered around the PIR sensing system 3. In this way, the detection range reinforces, and in many cases, teaches, the most accepted social distancing guidelines for preventing the spread of COVID-19.

Figure 5:
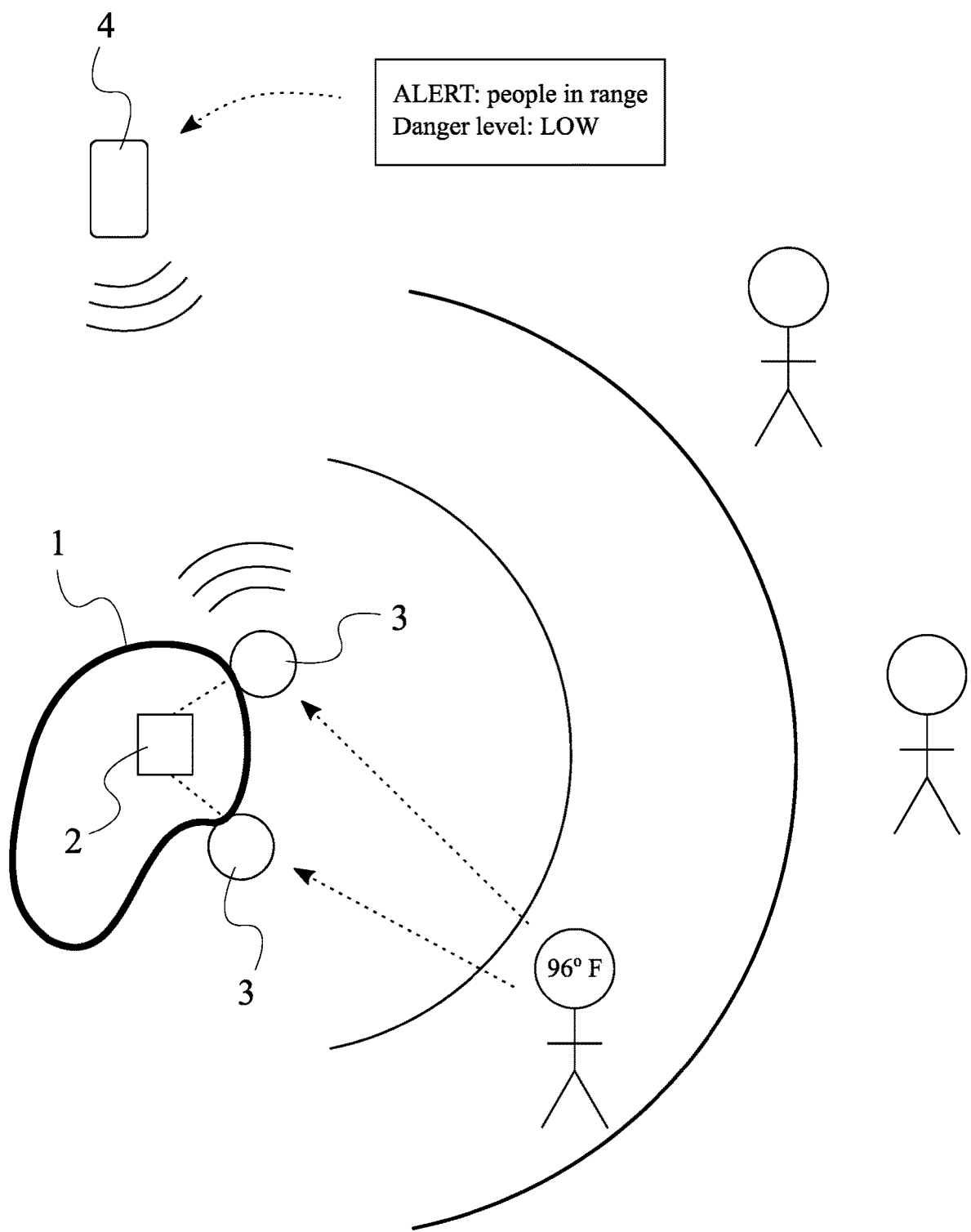
FIG. 5 is a schematic diagram illustrating the system of the present invention in a state of standard operation when a healthy individual is within the active range.
Figure 6:
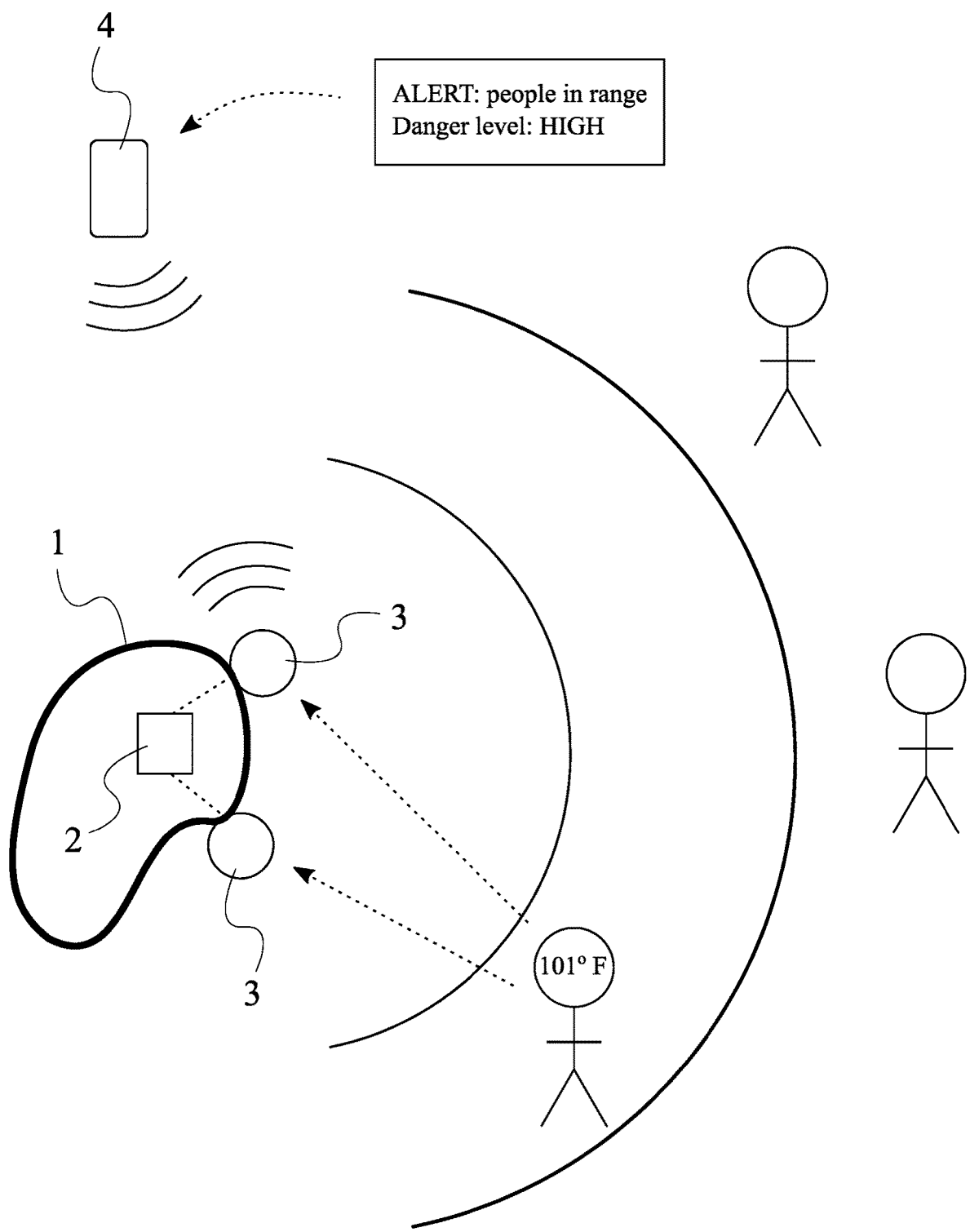
FIG. 6 is a schematic diagram illustrating the system of the present invention in a state of standard operation when an unhealthy individual is within the active range.

In many situations, the user benefits from the specific application of a set of PIR sensing units. To achieve this, the PIR sensing system 3 may include a pair of PIR sensor units, wherein the angle of operation is 240 degrees centered around the pair of PIR sensor units. In this embodiment, the wearable device 1 may relate to a belt, or to a set of units connected to wrist straps, as represented in FIGS. 5 and 6. This arrangement enables the PIR sensing system 3 to achieve higher measurement precision in a more applicable range around the user; namely, in front of the user.

The sensors of the PIR sensing system 3 are optimized within specific wavelengths that are advantageous for reading human heat signatures. Thus, the PIR sensing system 3 may be configured to detect a wavelength range between 8 micrometers to 12 micrometers. This wavelength range is generally most relevant when using the PIR sensing system 3 to determine the presence of human heat signatures.

In order to train an artificial intelligence to interpret heat signatures as being human or non-human, or as being above normal rather than normal, the artificial intelligence must be provided with a floor and ceiling of expected human heat signatures. To this end, a normal human temperature range may be set between 27 degrees Celsius and 36 degrees Celsius. While this indicates a wide range of temperatures on the low side of normal for human heat signatures, the range may help to bias an artificial intelligence into higher sensitivity toward high heat signatures.

Figure 4:
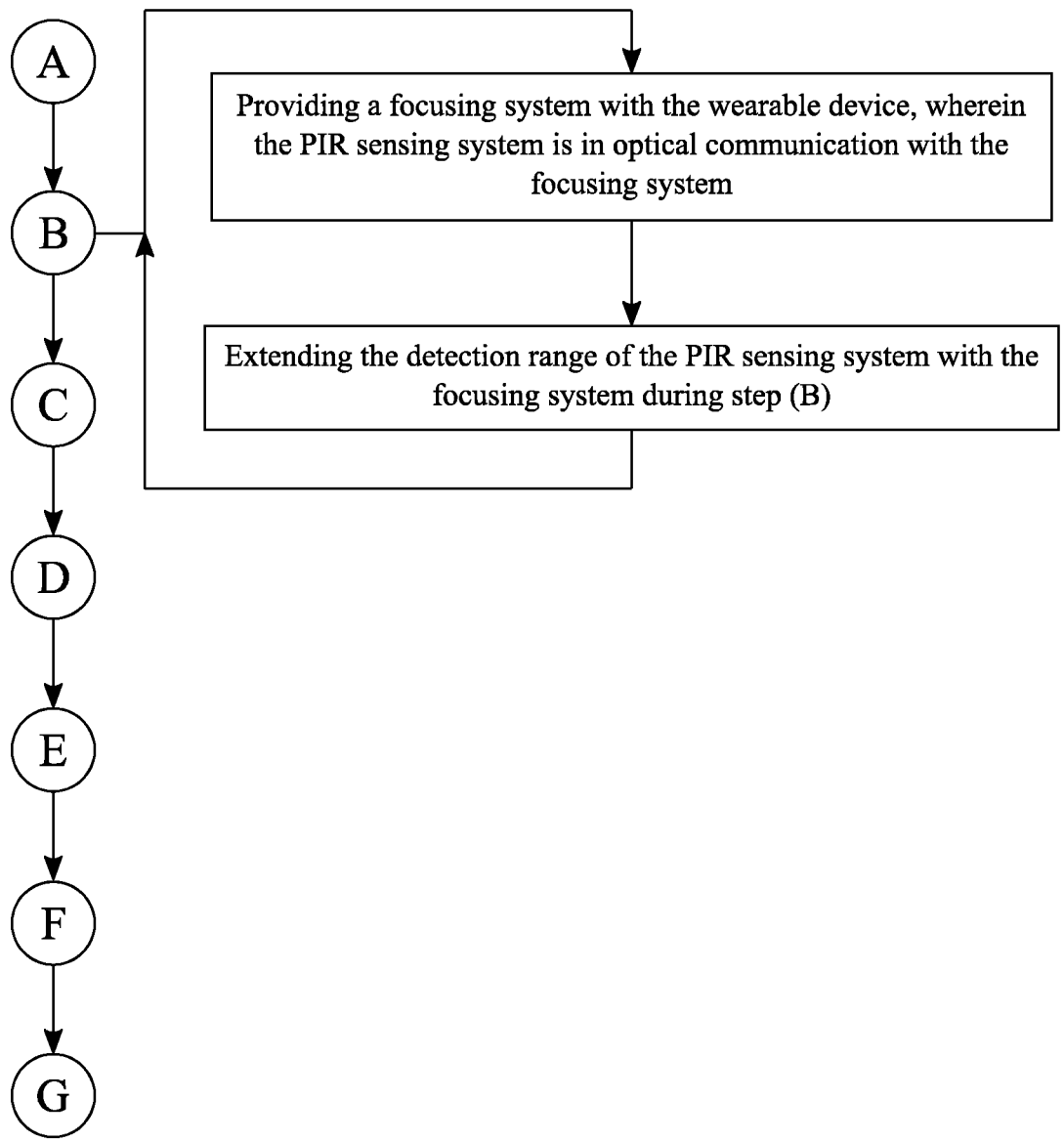
FIG. 4 is a flowchart illustrating the subprocess of extending the detection range of the PIR sensing system.

The PIR sensing system 3 relies upon detection of incident radiation through the emission of appropriate wavelengths to collect meaningful data regarding heat signatures and may benefit from increased range capabilities. Thus, a focusing system may be provided with the wearable device 1, wherein the PIR sensing system 3 is in optical communication with the focusing system, as represented in FIG. 4. The focusing system relates to a series of optical or thermal lenses capable of increasing the range of the PIR sensing system 3 by amplifying incident or outgoing photon wavelengths, thus enabling analysis of wavelengths from greater distances. The detection range of the PIR sensing system 3 is consequently extended with the focusing system during Step B. In this way, the PIR sensing system 3 is made more effective and efficient at reading distant and nearby thermal signatures.

There are many arrangements of focusing systems that are capable of improving detection of heat signatures as is relevant for the purposes of the present invention; however, it is relevant for the nature of this invention to provide a structure that is damage-resistant in outdoor conditions. To this end, in an exemplary embodiment of the present invention, the focusing system may be a flexible visual reflection system. The flexible visual reflection system is a device which enables improved photon manipulation properties of the PIR sensing system 3. The flexible visual reflection system further provides structural support during use of the present invention while simultaneously preventing damage to the PIR sensing system 3.

The lens utilized in amplifying incident waves to wavelengths that are more readily measurable by the PIR sensing system 3 must be highly effective at modifying incident or outgoing light to great distances. To achieve this, the focusing system may be a Fresnel lens. The Fresnel lens is optimized for long-distance light emission amplification and is thus often an ideal lens candidate for the present invention.

The present invention requires access to areas generally surrounding a user. To enable this access, the wearable device 1 may be configured to be worn by a waistbelt. In this way, the PIR sensing system 3 may be arranged with several sensors gathering data from all around the user.

It may be advantageous for a user to wear the present invention in locations other than upon a belt. To this end, the wearable device 1 may be configured to be worn by a wristband. Thus, the user of the present invention may direct the PIR sensing system 3 in relevant directions in order to actively gather data and may simultaneously benefit from incidental person detection as well.

Supplemental Description

Spiritual intelligence is the science of human energy management that clarifies and in the era of COVID-19 in which everywhere there is a panic like situation and according to the World Health Organization Social Distancing will be proven to be the only solution. In this research paper, an innovative localization method was proposing to track humans' position in an outdoor environment based on sensors is proposed. With the help of artificial intelligence, this novel smart device is handy for maintaining a social distancing as well as detecting COVID 19 symptom patients and thereby safety. In these COVID-19 environments, where everyone is conscious about their safety, we came up with the idea of this novel device. Most of the time, people on the roadside watched their front but were not able to look after what is going on behind them. The device will give alert to the person if someone in the critical range of six feet around him. The method is reasonably accurate and can be very useful in maintaining social distancing. The sensor model used is described, and the expected errors in distance estimates are analyzed and modeled. Finally, the experimental results are presented.

Some key words for the present invention include the following: sensor, WHO, social distancing, tracking, COVID-19, machine learning, python, smart device, artificial intelligence, and economical. A citation for the present invention is Rahul Reddy Nadikattu, Sikender Mohsienuddin Mohammad, and Pawan Whig, Novel Economical Social Distancing Smart Device for Covid19. International Journal of Electrical Engineering and Technology, 11(4), 2020, pages 204-217, which can be found at the following website address: http://www.iaeme.com/IJEET/issues.asp?JType=IJEET&VType=11&IType=4

1. INTRODUCTION

Intelligence Since COVID-19 spreads from individual to individual, diminishing the manners in which individuals come in close contact with one another is fundamental. Social separating implies staying at home, however much as reasonably expected, and maintaining a strategic distance [1-2]. From swarmed, open spots where close contact with others is likely, this is why remain at home requests are set up in such vast numbers of networks, dropping occasions and social affairs of more than ten individuals and shutting shops and café s, and bars. Its likewise why numerous schools have moved to web-based learning [3-7]. For essential excursions like shopping for food, the CDC suggests wearing a fabric face covering and remaining in any event 6 feet from others.

Humane removal is a primary method to hinder the spread of COVID-19. Also, it's significant that you follow the common removing suggestions in your locale, regardless of whether you're in one of the high-hazard gatherings or not.

It may with schools shut and individuals telecommuting, it might be enticing to get kids together for playdates or sleepovers or to feel that social occasions of more than ten individuals are protected [8-12]. In any case, social separating possibly works if we as a whole partake. Also, easing back down or forestalling the spread of the infection will spare lives.

The spread of COVID-19 has been the fast and bureaucratic, state, and neighborhood governments are doing whatever is essential to shield we all from becoming ill. While many people who become tainted will have indications like cold or seasonal influenza, and youngsters appear to be less influenced by the infection than grown-ups, we are liable for ensuring those at higher hazard [13-15]. Steps like social removing may feel like a burden. However, it's the ideal way right presently to secure our family, companions, and neighbors who might be helpless.

A coronavirus is a kind of typical infection that taints our upper respiratory tract framework, including throat and nose. It gets the name from its crown-like shape when watched under a magnifying instrument. According to the World Health Organization (WHO), pneumonia of obscure reason identified in Wuhan, China, was first answered to the WHO Country Office in China on 31 Dec. 2019. The episode was proclaimed a Public Wellbeing Emergency of International Concern on 30 Jan. 2020. On eleventh February 2020, WHO reported a name for the new coronavirus ailment: COVID-19. The circumstance was observed intently alongside day by day appraisal of the number of affirmed instances of COVID-19 over the globe. According to the WHO report, in the previous fourteen days, the name of the cases of COVID-19 outside China had expanded 13-crease, and the quantity of influenced nations significantly increased. With more than 1,18,000 cases in 114 countries and 4,291 individuals who have lost their lives, COVID-19 was spreading alarmingly.

In the resulting days and weeks ahead, it expected that the number of cases, the number of passing's, and the quantity of influenced nations would increment further. Therefore, the WHO described COVID-19 as a pandemic [16-18]. It spreads through the novel Corona Virus.

The number of people been infected with this deadly disease is increasing in India & the USA also. WHO has taken active steps intending to curb the spread of this disease? As per an advisory issued the suspected patient should look for the following signs and symptoms:
Fever
Cough
Shortness of breath or difficulty in breathing Presently there is no medicine to cure or vaccine to prevent COVID-19. As they say, prevention is better than cure, is aptly suitable in the current scenario. The best ways to avoid infection is to get exposure to the virus through the following measures:
Observe good personal Hygiene
Practice frequent hand washing with soap
Covering mouth when coughing and sneezing
Social Distancing As per Health Experts, Social Distancing can be an effective measure to curtail the spread of COVID-19. Social distancing is purposely maintaining the physical space between individuals to prevent the spread of illness. Keeping some distance of at least one meter from other people lessens the chances of getting infected with COVID-19. Social distancing is a prevention and control intervention implemented to decrease contact between those infected with a disease-causing pathogen and to slow down the rate and extent of disease transmission in a community [19]. For the practical impact of social distancing, the authorities have also taken the following steps:
Work from home
Closing of Educational Institutions and Coaching centers and shifting to online mode
Maintaining in touch with near and dear ones using audio and video calls
Annulling or deferring meetings, seminars, and conferences There may be instances where people's movement or traveling is necessary to provide essential services like food, medicine, hospitals, banks, etc. Social distancing in such scenario can be in the following manner:
Keeping a distance of at least 1-1.5 meter between individuals
Greet people with Namaste instead of handshakes
Usage of electronic money instead of currency
Avoid public transport
Maintaining a distance of at least 1-1.5 meter while standing in a queue for shopping The individuals who are staying at home should take the following precautions:
Wash hands frequently with soap
Request visitors to avoid coming home
Avoid visiting markets and shops for buying essentials and prefer the home delivery option
Frequently sanitize surfaces like doorknobs, taps, kitchen surfaces and other objects that are touched on a regular basis Technology will effectively be used for maintaining the requisite distance as per social distancing norms [20]. The proposed system uses a wearable device capable of sensing the distance between two individuals and triggering an alarm in the event of proximity between the individuals.

2. BLOCK DIAGRAM OF SYSTEM

The wearable device consists of PIR Sensor, microcontroller, and mobile for display and gives alert to the user.

Figure 7:
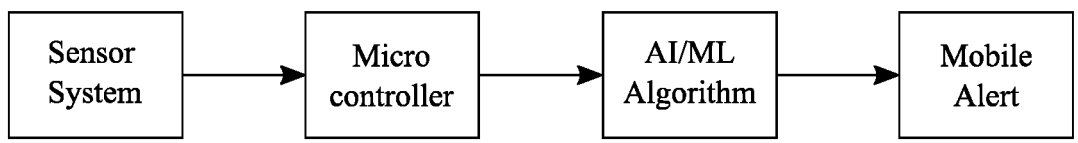
FIG. 7 is a flowchart illustrating an overview of the process of sending a mobile alert.

The sensor will detect the distance between the wearer and other individuals. The micro-controller is programmed to verify the desired length and trigger the alarm as well as give the mobile alert to the user. The proposed system is shown in FIG. 7.

PIR Sensor is also called Passive Infrared Sensors. These sensors are used to detect human movement when it comes in a particular range. The range of coverage depends upon the type and design of the sensor.

The PIR sensor does not radiate energy to space on the other hand its working relies on receiving infrared radiation from the human body to make an alert into mobile device. The temperature of the normal human body is 36-27° C., and most of its radiant energy concentrated in the wavelength range of 8-12 µm. If the human infrared radiation directly irradiated on the radar, it will cause a temperature change to output a signal. Still, in doing so, the detection distance will not be far. To lengthen the detector's detection distance, an optical system must be added to collect the infrared radiation, using a flexible visual reflection system or a Fresnel lens, which is made of plastic as a focusing system for IR radiation.

Technology In the location territory, the infrared radiation vitality of the human body through the attire got by the focal point of the indicator and spotlight on the pyroelectric sensor. The human body (gatecrasher) will move in this observation mode; it moves to a specific field of view and leaves the field of view. The pyroelectric sensor sees the moving human body for some time and afterward does not see it, so the human body. The IR radiation continually changes the pyroelectric material's temperature with the goal that it yields a relating signal, which is the alert sign.

The various features of different types of PIR Sensors with their angle of operation and the direction ranges are given in Table 1.

TABLE 1

Features of Different types of PIR Sensor

| Product | Measuring range (theoretical value) | Features |
|---|---|---|
| Grove - PIR Motion Sensor | Max Distance: 3-6 m (3 m by default) Angle < 120 deg | Measuring distance and holding time adjustable response speed: .3-25 s |
| Grove - Adjustable PIR Motion sensor | Max Distance: 3-6 m Angle: X = 110 deg Y = 90 deg | Measuring distance and holding time adjustable |
| Grove - mini PIR motion sensor | Max Distance: 2-5 m (2 m by default) Angle: X = 11 deg Y = 90 deg | Sensitivity adjustable mini-size |
| PIR Motion Sensor - Large Lens version | Max Distance: 9 m Angle: <120 deg | Large lens which can support long range and wide angle 2.54 mm standard connector |
| PIR Motion sensor module | Max Distance: 3-7 m Angle: < 120 deg | Measuring distance adjustable |
| Mini PIR Motion Sensor Module | Max Distance: 7 m Angle: <100 deg | Mini-size |

There is various micro-controller available like Arduino and raspberry pie. The architecture of Arduino given below with the pin description. The simulation of the device was done using the Arduino micro-controller, and the actual design was realized using raspberry pie.

TABLE 2

| Microcontroller | |
|---|---|
| 1 | Power USB |
| 2 | Power (Barrel Jack) |
| 3 | Voltage Regulator |
| 4 | Crystal Oscillator |
| 5, 17 | Arduino Reset |
| 6, 7, 8, 9 | Pins (3.3,5, GND, Vin) |
| 10 | Analog pins |
| 11 | Main microcontroller |
| 12 | ICSP pin ( ) |
| 13 | Power LED indicator |
| 14 | TX and RX LEDs |
| 15 | Digital I/O |
| 16 | AREF |
| 12 | ICSP pin ( ) |

3. WORKING OF DEVICE

The proposed device based on the principle of a PIR sensor on receiving infrared radiation from the human body to make an alarm and alert on the mobile device. Also, calibrating the infrared radiation received from the sensor into the thermal conductivity temperature of the body can be calculated. This way, the device will measure not only social distancing but also the heat of the person in the range. Using a machine learning algorithm, it detected that the person has COVID-19 symptoms or not. Any object with temperature is always radiating infrared rays to the outside world. Usually, the surface temperature of the human body is 36-27° C., and most of its radiant energy concentrated in the wavelength range of 8-12 µm. In this novel device, a pair of PIR sensors are used, which will cover almost 240° around the wearable, and based on radiating infrared rays, it will produce an alert to the wearable. The extension of this device using artificial intelligence and machine learning also alerts the possibility of corona patients around you. The total angle covered around the wearable shown indicates the device will include 240° around the wearable.

When someone comes in the critical range of social distancing, then an alert has been initiated in the mobile of the person and then using ML algorithm advice has been issues that "Someone behind you" also based on the temperature of the body the probability of symptoms of COVID calculated.

4. MATHEMATICAL MODELING

The device follows photometry inverse law. The simple equation for measuring distance x and the angle of incidence θ with target surface:

$$S(x, \theta) = \frac{\alpha}{x^2} \cos\theta + \beta$$

... wherein $S(x, \theta)$ is the sensor output; x is distance; θ is the angle of incidence with target surface; α and β are the sensor model parameters; a depends upon radiant intensity of material of sensor, spectral sensitivity of photodiode used, gain of amplifier and reflectivity coefficient of target; and β is the parameter which depends upon amplifier offset plus ambient light effect to minimize the effect of β equation 1 can be written as:

$$y(x, \theta) = S(x, \theta) - \beta = \frac{\alpha}{x^2}\cos\theta$$

... using above equation, the distance of the person can be calculated. From the previous equation:

$$x = \sqrt{\frac{\alpha}{y}\cos\theta} = \sqrt{\frac{\alpha}{y}}\sqrt{\cos\theta}$$

Let two PIR sensor measuring flat surface with an angle of incidence $\theta$ and value of $y_1$ can be calculated if value of $\theta$:

$$x'_1 = \sqrt{\frac{\alpha}{y_1}}$$

$$x'_2 = \sqrt{\frac{\alpha}{y_2}}$$

... using Snell's law, the ratio of two incident angle is calculated as:

R'=tan θ' and R=tan θ

... where $\theta$ is the actual angle of incidence and $\theta'$ is the apparent angle of incidence.

The relationship between R and R' is:

R=R'$\sqrt{\cos\theta}$

... and hence to obtain $\theta$ the following equation must be solved:

R'(cos θ)$^3$+(cos θ)$^2$-1

Figure 8:
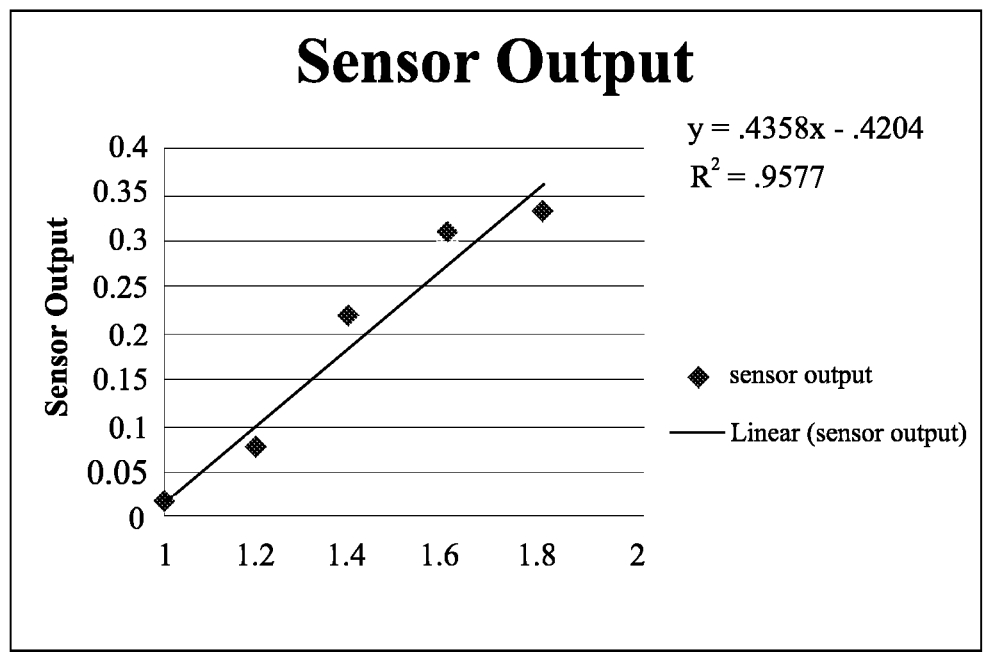
FIG. 8 is a graph between the sensor output and distance.

... with the different value of $\theta$ taking from range −120 to 120 and R' a line is fitted with a coefficient of correlation 0.95 and having standard error of 0.583019 by considering the typical values of $\alpha$=0.7 and $\beta$=0.01. The graph between the sensor output and with distance is shown in FIG. 8.

Figure 9:
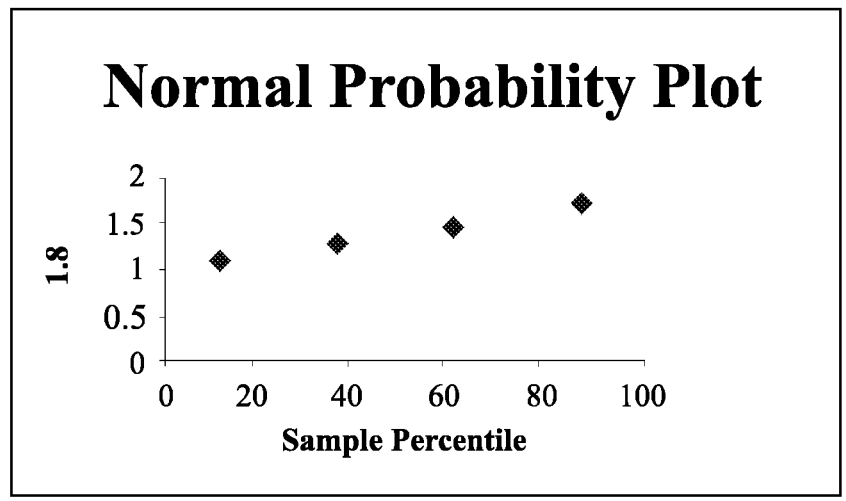
FIG. 9 is a graph of normal probability for the sensor.

There is a specific case for the likelihood plot, which is known as the standard likelihood plot. It is a graphical technique used to check the ordinary appropriation of the information. On plotting the focuses, a roughly straight line framed, which shows that typical circulation is a nice model for a given arrangement of information of sensor yield and the separation of the individual. The standard likelihood plot for the framework is plotted and appeared in FIG. 9.

It is also called lingering plot. A lingering plot is a plot between a yield and information factors used to show whether the given relapse model is proper as indicated by your information. There ought not be any unmistakable example for the plotted residuals, and they should be arbitrary. Great relapse models by and large get uncorrelated residuals. The remaining plot for the created framework has arranged and appeared in FIG. 10.

In the relapse measurements of a gadget has been done and appeared in Table 2. The table incorporates various estimations of numerous R, R square, and balanced R square, the standard blunder as acquired from the examination. The measure of R Square shows the straight relationship of one boundary concerning others. The Value of R-Square is exceptionally near solidarity demonstrates that the extent of the change of one variable is unsurprising from the other variable.

The standard mistake is the distinction in the estimation of the genuine and assessed variable. The least the measure of standard mistake shows how close the genuine and anticipated worth is or the gadget's affectability. The expense of the standard blunder is little, which shows a superior precision of the gear.

TABLE 3

| Regression Statistics | |
|---|---|
| Multiple R | .990993 |
| R Square | .982068 |
| Adjusted R Square | .973102 |
| Standard Error | .042346 |
| Observations | 14 |

Inferences from Table 3 include the following:
(a) The value of $R^2$ in the case of a sensor model which shows the direction of a linear relationship between the distance between the persons and sensor output.
(b) The value of standard error found to be smaller, which shows better accuracy of the model.

The ANOVA analysis for the device presented in Table 4. The ANOVA examination is a straightforward investigation of change on information for at least two factors. The ANOVA table gives the accompanying data: degrees of opportunity (df), the sum of the squares (SS), the mean square (MS), the F proportion (F), the significance (S).

ANOVA examination is basic to test the theory for each example esteem with a similar likelihood dissemination. A high F esteem speaks to there is an insignificant deviation between the methods. The measure of ways is the equivalent, which prompts minimal estimation of standard blunder, and the gadget is sensibly precise.

TABLE 4

| ANOVA Analysis | | | | | |
|---|---|---|---|---|---|
| ANOVA | Df | SS | MS | F | SignificanceF |
| Regression | 1 | .196414 | .196414 | 109.531 | .009007 |
| Residual | 2 | .003586 | .001793 | | |
| Total | 3 | .2 | | | |

5. DEVICE SIMULATION AND RESULT

Figure 10:
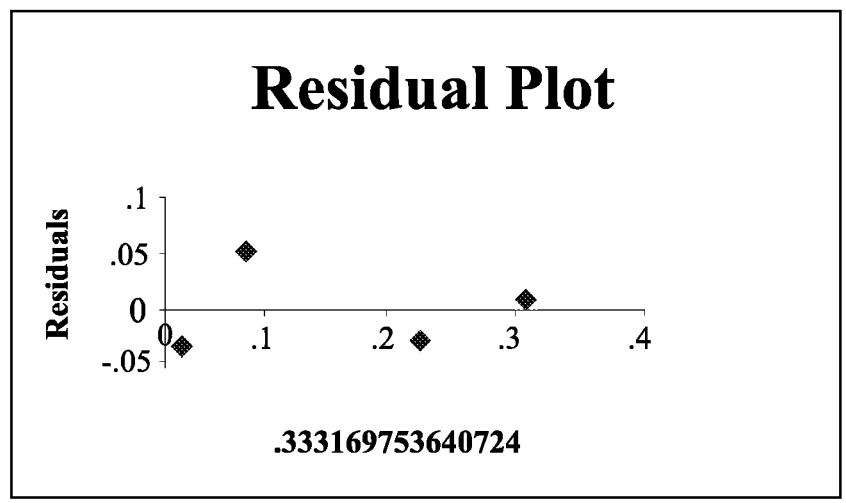
FIG. 10 is a graph of the residual plot for the device.

The hardware implementation for the social distance monitoring system is shown in FIG. 10. The simulation of the device has done, and the results found to be within range. The real-time simulation of the device using a microcontroller and sensor is shown in FIG. 11. It is shown that when someone comes inside the critical field of six feet, the alert will be given on the mobile with the indication that whether a person in the range having COVID symptoms or not. On plotting a trend line between sensor output and distance, the coefficient of determination R2 found to be 0.95, which is close to 1. It shows that the regression line is an excellent fit to the data. The standard probability and residual plot for the system are given in FIG. 9 and FIG. 10. Both plots validate that the regression model obtained is appropriate, and thus accuracy of the system is verified. The system has excellent skills and is less complicated. The system is highly suitable for maintaining social distance and detecting COVID symptom patients.

6. CONCLUSION

This advantage of this novel device is that it does not only help in maintaining social distancing but also give alert whether person in a range having COVID symptoms or not. The accuracy of the device can be increased by improving the design of the sensor. This research study will help researchers working in the same field.

Although the invention has been explained in relation to its preferred embodiment, it is to be understood that many other possible modifications and variations can be made without departing from the spirit and scope of the invention as hereinafter claimed.

What is claimed is:

1. A method of maintaining social distancing guidelines with surrounding persons, the method comprising the steps of:
   - (A) providing a wearable device and a portable computing device, wherein the wearable device comprises a microcontroller and a passive infrared (PIR) sensing system, and wherein a normal human temperature range is stored on the microcontroller;
   - (B) monitoring a surrounding area of the wearable device with the PIR sensing system in response to the surrounding area being within an angle of operation and a detection range of the PIR sensing system;
   - (C) converting at least one thermal signature into a body temperature reading with the microcontroller in response to the thermal signature being detected within the surrounding area by the PIR sensing system;
   - (D) relaying a surrounding person alert from the wearable device to the portable computing device in response to the thermal signature being detected within the surrounding area by the PIR sensing system;
   - (E) relaying a high-risk-of-sickness addendum from the wearable device to the portable computing device in response to the body temperature reading being outside of the normal human temperature range;
   - (F) relaying a low-risk-of-sickness addendum from the wearable device to the portable computing device in response to the body temperature reading being inside of the normal human temperature range; and
   - (G) outputting, with the portable computing device, the surrounding person alert with either the high-risk-of-sickness addendum or the low-risk-of-sickness addendum.

2. The method as claimed in claim 1, wherein the detection range is a six-foot radius centered around the PIR sensing system.

3. The method as claimed in claim 1, wherein the PIR sensing system includes a pair of PIR sensor units, and wherein the angle of operation is 240 degrees centered around the pair of PIR sensor units.

4. The method as claimed in claim 1, wherein the PIR sensing system is configured to detect a wavelength range between 8 micrometers to 12 micrometers.

5. The method as claimed in claim 1, wherein the normal human temperature range is between 27 degrees Celsius and 36 degrees Celsius.

6. The method as claimed in claim 1 comprising the steps of:
   providing a focusing system with the wearable device, wherein the PIR sensing system is in optical communication with the focusing system; and
   extending the detection range of the PIR sensing system with the focusing system during step (B).

7. The method as claimed in claim 6, wherein the focusing system is a flexible visual reflection system.

8. The method as claimed in claim 6, wherein the focusing system is a Fresnel lens.

9. The method as claimed in claim 1, wherein the wearable device is configured to be worn by a waistbelt.

10. The method as claimed in claim 1, wherein the wearable device is configured to be worn by a wristband.

* * * * *